United States Patent [19]

Schröder et al.

[11] Patent Number: 4,652,092
[45] Date of Patent: Mar. 24, 1987

[54] NEODYMIUM-YAG LASER, FOR OPHTHALMOLOGICAL TREATMENT

[75] Inventors: Eckhard Schröder, Eckental; Reinhardt Thyzel, Heroldsberg, both of Fed. Rep. of Germany

[73] Assignee: Meditec-Reinhardt Thyzel GmbH, Heroldsberg, Fed. Rep. of Germany

[21] Appl. No.: 752,189

[22] PCT Filed: Oct. 29, 1984

[86] PCT No.: PCT/DE84/00227
§ 371 Date: Jun. 27, 1985
§ 102(e) Date: Jun. 27, 1985

[87] PCT Pub. No.: WO85/01870
PCT Pub. Date: May 9, 1985

[30] Foreign Application Priority Data
Oct. 29, 1983 [DE] Fed. Rep. of Germany ....... 3339369

[51] Int. Cl.⁴ ...................... G02B 13/00; G02B 17/00; G02B 27/00
[52] U.S. Cl. .................................................. 350/463
[58] Field of Search ............... 350/463, 438, 453, 415, 350/172

[56] References Cited
U.S. PATENT DOCUMENTS
3,817,604 6/1974 Watt ..................................... 350/232
4,203,652 5/1980 Hanada ............................... 350/453
4,499,897 2/1985 Roussel ............................... 350/438
4,592,625 6/1986 Uehara et al. ....................... 350/415

FOREIGN PATENT DOCUMENTS
2713907 5/1978 Fed. Rep. of Germany .

Primary Examiner—John K. Corbin
Assistant Examiner—Rebecca D. Gass
Attorney, Agent, or Firm—Thomas Schneck

[57] ABSTRACT

A neodymium-YAG laser is described, which can be used for ophthalmological treatment. The laser has a laser beam guide, in which the laser beam is guided as a parallel beam over a long distance and following the latter is focused onto the operating plane by a focusing optics.

According to the invention, an afocal system with a plurality of optical components is placed in the parallel optical path at a distance of more than approximately 50 cm from the focusing optics. This afocal optical system substantially does not influence the beam in its normal position. As a result of an optical component in the afocal system, which is displaceable, it is possible to vary the angle of the marginal beams of the focused beam.

According to the preferred embodiment, the afocal system has two single lenses, whereof one has a positive and the other a negative refractive power and one is displaceable.

8 Claims, 1 Drawing Figure

NEODYMIUM-YAG LASER, FOR OPHTHALMOLOGICAL TREATMENT

TECHNICAL FIELD

The invention relates to a neodymium-YAG laser for ophthalmological treatment.

BACKGROUND

Neodymium-YAG lasers with laser beam guides and focusing optics are used for operations on the human eye. Since in the case of such operations, the so-called optical opening is larger than the laser beam spot, hitherto no attention has been paid to the variation in the spot size and consequently also to the associated variation in the angle of the marginal beams of the focused beam, i.e. the variation of the so-called divergence angle. Thus, known neodymium-YAG lasers are constructed in such a way that the laser beam is focused with a given fixed divergence angle.

DISCLOSURE OF THE INVENTION

However, it has been recognised that for safety reasons it would be desirable to be able to vary the angle of the marginal beams of the focused beam, i.e. to vary the divergence angle. Thus, the divergence angle should be as large as possible, so that there is a rapid decrease in the energy density of the operating beam upstream and downstream of the operating plane in the eye on which the laser is focused.

However, the angle of the marginal beams is limited by the size of the pupil. In order to be able to operate with the maximum possible divergence angle in all cases, it will be necessary to vary the angle and consequently vary the spot size of the focus. The displacement of the focal plane of the focused beam must thereby be as small as possible.

In the case of argon lasers, it is known to adjust the spot size without displacing the focal plane using zoom optics, which is very complicated and costly.

However, in the case of neodymium-YAG lasers, such zoom optics are not only undesirable for cost reasons, but also for the following reasons. When using neodymium-YAG lasers as operating lasers, whose light is not visible, a helium-neon laser is frequently additionally used as the collimating or target laser. As the beam of the helium-neon laser is to be focused in the same plane as the beam of the neodymium-YAG laser, it is necessary to bring about a very good color correction of the zoom optics over a wide range, so that its construction is necessarily very complicated.

The object of the invention is to bring about simple optical beam guidance for a neodymium-YAG laser, which permits an adjustment of the divergence angle without any detectable displacement of the focal plane.

Using a neodymium-YAG laser with a laser beam guide in which the laser beam is guided as a parallel beam over a long distance and with focusing optics which focus the laser beam onto the operating plane following the distance, this object is met by placing an afocal system with a plurality of optical components in the parallel beam path at a distance of more than about 50 cm from the focusing optics. In its normal position the afocal system substantially brings about no change to the parallel beam. An optical component in the afocal system is displaceable for varying the angle of the marginal beams of the focused beam.

In most neodymium-YAG lasers used for ophthalmological treatment, for some reason or the other such as, for reflecting into the optical path of a slit lamp, the laser beam is guided over a long distance often for more than 1 meter and is only then focused in the human eye.

In the case of a neodymium-YAG laser with such a beam guidance, the divergence angle can easily be made adjustable in that an afocal system is placed in the parallel optical path at an adequate distance in front of the focusing optics. In its normal position, this afocal system does not modify the parallel beam, i.e. the diameter thereof. It is sufficient for increasing or decreasing the divergence angle to move one of the two optical components of this additionally introduced system slightly out of the normal position, in which said system is afocal. As a result of this small movement of one of the two components, the parallel beam is no longer imaged in a parallel beam and instead the latter leads to a slightly convergent or divergent beam. As a result of the long distances exceeding roughly 0.5 m, there is a slight aperture increase as a result of the very small angular change and consequently a large variation of the divergence angle, as well as a variation of the spot size. The displacement of the focal plane is within the depth of focus of the measuring microscopes and can therefore be ignored.

Further advantages are gained by the following alternate embodiments of the invention.

The optical component used for varying the angle of the marginal beams can be continuously displaceable, so that the divergence angle can also be continuously set over a wide range.

However, in practice, the more easily realisable construction is often adequate in which there are only three positions of the optical component which modifies the divergence angle. These consist of a central position for normal operation, a position in which the divergence angle is reduced compared with the central position and a position for large divergence angles which also require large pupillary apertures.

It is in all cases advantageous if the optical component is motor-displaced, because particularly in the case of eye examining units, the neodymium-YAG laser and the optical components provided for controlling the divergence angle are not positioned within the reach of the operator. Such motor-operated adjustments, such as microswitches or other components for determining the position of the displaceable optical component, are known in the art.

In another embodiment, a semireflecting or wavelength-selective mirror is positioned in front of the afocal system and permits the reflecting in of a laser beam of a helium-neon laser, which is used as the collimating or image-forming beam.

It is particularly surprising that the afocal system can be a system comprising two single lenses, which not only images the beam of the neodymium-YAG laser with a wavelength of 1.06 $\mu$m, but also the beam of the helium-neon laser with a wavelength of 633 nm, without any further correction and without displacement of the focal plane.

An additional optical system expands the optical path to the requisite operating diameter, after the optical path has been guided over a considerable distance as a parallel or slightly divergent/convergent bundle with a relatively small diameter. This makes it possible to significantly reduce the diameter of the laser beam guide.

BRIEF DESCRIPTION OF THE DRAWING

The FIGURE is a plan view of the apparatus of the present invention.

BEST MODE FOR CARRYING OUT THE INVENTION

Figure 1:
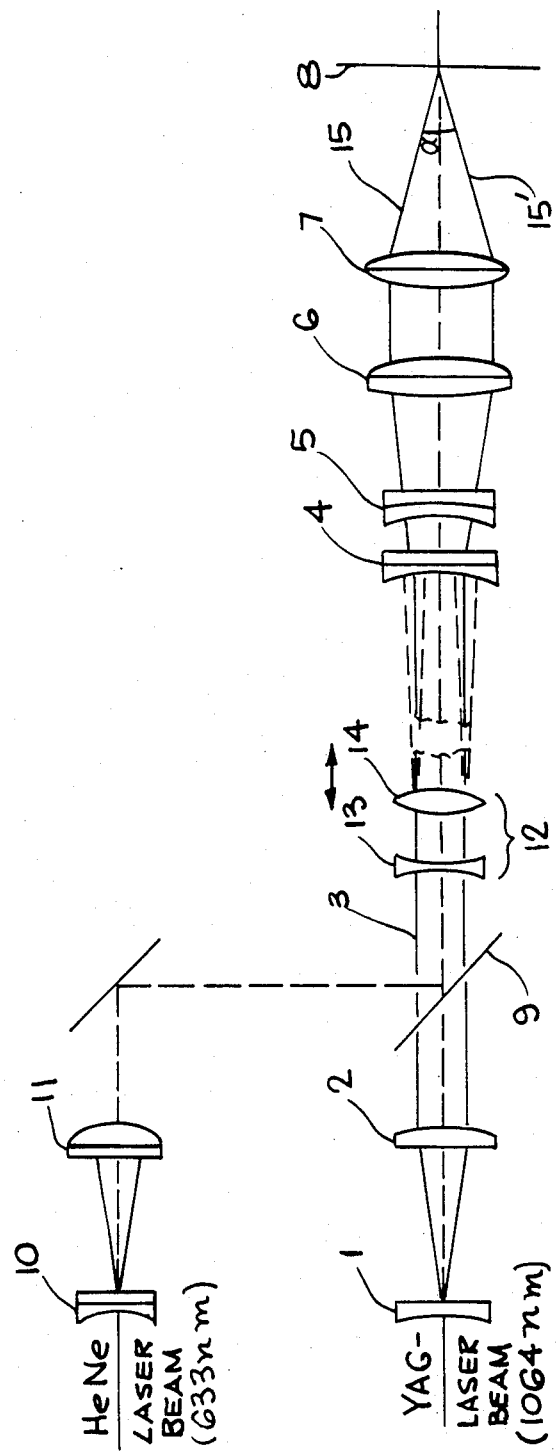

With reference to the FIGURE the neodymium-YAG laser beam is expanded by lenses 1 and 2 and is guided as a parallel beam 3 over a long distance, such as 2 meters. The beam is then again expanded by the optical components 4, 5, 6, which for colour correction purposes are achromatic cemented components and is subsequently focused by component 7 onto an operating plane 8, such as the fundus oculi of a human eye.

The beam of a helium-neon laser expanded by the cemented components 10, 11 is reflected in the area of the first parallel beam guide 3 of the YAG-laser beam by means of a semireflecting or color-selective mirror 9 and is used as a collimating beam. The term color-selective mirror is understood to mean a mirror, which transmits light of the wavelength of the neodymium-YAG laser (1064 nm), but reflects the light of the wavelength of the helium-neon laser (633 nm).

This optical arrangement described above, is known and is used in YAG-laser OPL 4 of Meditec Reinhardt Thyzel GmbH, 8501 Heroldsberg, Germany. Express reference is made to the construction and the possible uses of this known laser.

According to the invention, an afocal system 12 comprising a positive lens 13 and a negative lens 14 is placed in the vicinity of the parallel beam guide 3 of the YAG-laser beam between mirror 9 and cemented component 4 and at a distance of more than 50 cm from the latter. In its normal position, the afocal system 12 substantially makes no change to the parallel optical path, i.e. the diameter of the parallel beam.

As a result of a displacement of either positive lens 13 or negative lens 14, the parallel beam is imaged as a slightly convergent or divergent bundle. As a result of the considerable distance covered by the beam prior to further expansion and focusing, the most minor angular modifications lead to a large increase or decrease in the aperture and consequently to a large change in the divergence angle, i.e. the angle $\alpha$ formed by the marginal beams 15, 15' of the focused beam. The focus change can be ignored and is within the depth of focus of the measuring microscope for the image-forming process with which the operating plane, in the human eye is checked.

The further expansion of the beam by components 4, 5 and 6 has a positive influence on the divergence angle variation achievable at a given distance.

Thereby, in the case of a given diameter of the parallel beam and given distance between the focusing lens group/operating plane and whilst respecting boundary conditions such as the length of the beam, the specialist is immediately in a position to calculate the afocal system and the displacements of one component of this system necessary for bringing about a given change in the divergence angle.

Furthermore, the system provided according to the invention is also suitable for modifying the spot size and by slight defocusing of the laser beam and modifying the divergence angle, it is possible to vary the diameter of the beam, e.g. in the plane of the fundus oculi. The diameter change can easily be checked by means of the helium-neon collimating laser beam.

We claim:

1. Neodymium-YAG laser, particularly for ophthalmological treatment, with a laser beam guide, in which the laser beam is guided as a parallel beam over a long distance, and with a focusing optics, which focuses the laser beam onto the operating plane following said distance, the focussed laser beam having marginal beams converging at an angle, characterized in that an afocal system (12) with a plurality of optical components (13, 14) is placed in the parallel beam path (3) at a distance of more than approximately 50 cm from the focusing optics (7), said optical components being in the vicinity of a normal position, said normal position defined as that position in which said afocal system brings about substantially no change to the parallel beam when in said normal position but varying the angle ($\alpha$) of the marginal beams (15, 15') of the focused beam upon displacement of one of the optical components from said normal position.

2. Laser according to claim 1, characterized in that a wavelength-selective mirror (9) is positioned in front of the afocal system, and with a helium-neon laser beam directed onto said mirror, said beam having said wavelength for use as a collimating beam.

3. Laser according to claim 1, characterized in that the afocal system comprises two single lenses (13, 14), one having a positive and the other a negative refractive power and wherein one is displaceable.

4. Laser according to claim 1, characterized in that a further optical system expands the beam after the beam emerges from the afocal system.

5. Laser according to claim 1, characterized in that one of the optical components (13, 14) is displaceable for varying the angle ($\alpha$) of the marginal beams (15, 15') to either of two positions relative to said normal position, said two positions being on opposite sides of the normal position.

6. Laser according to claim 5, characterized in that a motor with a control unit is provided for the displacement of said displaceable optical component (13, 14).

7. Apparatus for adjusting the convergence angle for a focused laser beam originating as a parallel beam comprising,
   a parallel laser beam aimed at a target,
   a focussing lens proximate to said target for causing beam convergence onto said target at an angle of convergence,
   an afocal lens system having a positive and a negative lens pair placed in the parallel laser beam path at a normal position, said normal position defined as that position in which said afocal lens system brings about substantially no change in the parallel laser beam, said lens pair having means for relative motion of the lenses toward and away from each other relative to the normal position of said lens pair, thereby increasing and decreasing said angle of convergence, said lenses being achromatic relative to light from a neodymium-YAG laser and a helium-neon laser.

8. The apparatus of claim 7 wherein said means for relative motion provides two positions on either side of the normal position, including a first position in which the angle of convergence is increased and a second position in which the angle of convergence is decreased.

* * * * *